(12) United States Patent
Fetzer et al.

(10) Patent No.: US 7,637,163 B2
(45) Date of Patent: Dec. 29, 2009

(54) THIN-FILM ULTRASONIC PROBE

(75) Inventors: Barry A. Fetzer, Renton, WA (US); Fred D. Young, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 686 days.

(21) Appl. No.: 11/345,904

(22) Filed: Feb. 2, 2006

(65) Prior Publication Data

US 2007/0239018 A1    Oct. 11, 2007

(51) Int. Cl.
*G01N 29/28* (2006.01)
*G01N 29/24* (2006.01)
*G01N 29/06* (2006.01)

(52) U.S. Cl. ...................................................... 73/644
(58) Field of Classification Search ................... 73/636, 73/644
See application file for complete search history.

(56) References Cited

U.S. PATENT DOCUMENTS

| | | | | |
|---|---|---|---|---|
| 2,992,553 | A * | 7/1961 | Joy | 73/636 |
| 3,960,005 | A * | 6/1976 | Vezina | 73/614 |
| 3,962,908 | A * | 6/1976 | Joy | 73/636 |
| 4,088,028 | A * | 5/1978 | Hildebrandt | 73/611 |
| 4,098,132 | A * | 7/1978 | Mikesell | 73/639 |
| 4,563,900 | A * | 1/1986 | Harada et al. | 73/644 |
| 5,454,269 | A * | 10/1995 | Vogt | 73/644 |
| 5,549,001 | A * | 8/1996 | Brokowski et al. | 73/597 |
| 5,585,565 | A * | 12/1996 | Glascock et al. | 73/644 |
| 5,814,731 | A * | 9/1998 | Alexander et al. | 73/644 |
| 7,284,434 | B1 * | 10/2007 | Fleming | 73/644 |
| 7,320,249 | B2 * | 1/2008 | Georgeson et al. | 73/634 |
| 7,395,714 | B2 * | 7/2008 | Georgeson et al. | 73/634 |
| 2004/0003664 | A1 * | 1/2004 | Ishikawa et al. | 73/644 |
| 2006/0065055 | A1 * | 3/2006 | Barshinger et al. | 73/609 |
| 2007/0175282 | A1 * | 8/2007 | Fetzer et al. | 73/649 |

OTHER PUBLICATIONS

Innovation in NDT™ brochure, p. 19, printed Aug. 2004.
Innovation in NDT™ "Olympus NDT—Phased-Array Probes—Immersion Probes," www.rd-tech.com/paprobes_immersion.html.
Innovation in NDT™ "Olympus NDT—Phased Array Probes—Contact Probes," www.rd-tech.com/paprobes_contact.html.
NDT Solutions Ltd, "Ultrasonic Wheel Probes," www.ndtsolutions.com/wheel.htm.

(Continued)

*Primary Examiner*—Hezron Williams
*Assistant Examiner*—Rose M Miller (57) ABSTRACT

An ultrasonic probe for examining an item. The probe includes a body having a contact surface adapted for contacting the item when being examined and an ultrasonic transducer attached to the body and spaced from the contact surface. The probe further includes a spacer positioned in the body between the transducer and the contact surface for spacing the transducer from the item when being examined. The spacer includes a coupling surface facing the item when being examined and a transducer surface facing the transducer. The probe also includes a fluid outlet positioned adjacent the coupling surface of the spacer for delivering coupling fluid to the coupling surface as a film so that the coupling fluid tends to maintain contact with the spacer due to surface tension after the fluid is delivered through the outlet.

21 Claims, 5 Drawing Sheets

OTHER PUBLICATIONS

Innovation in NDT™ "Olympus NDT—Phased-Array Probes—Angle Beam Probes with External Wedges," www.rd-tech.com/paprobes_anglebeam.html.

Innovation in NDT™ "Olympus NDT—Phased-Array Probes—What are Phased-Array Probes?," www.rd-tech.com/paprobes.html.

Innovation in NDT™ "Olympus NDT—Phased-Array Probes—Angle Beam Probes with Internal Wedges," www.rd-tech.com/paprobes_anglebeamint.html.

Innovation in NDT™ "Contact Ultrasonic Transducers," www.panametrics-ndt.com/ndt/ndt_transducers/contact/index.html.

Innovation in NDT™ "Ultrasonic Couplants," www.panametrics-ndt.com/ndt/ndt_technology/ultrasonic_couplants.html.

Innovation in NDT™ "Olympus NDT—Angle Beam Testing and 0 Degree Testing," www.rd-tech.com/tech_ultra_angle.html.

Innovation in NDT™ "Olympus NDT—Aqualene Couplant," www.rd-tech.com/couplant.html.

* cited by examiner

THIN-FILM ULTRASONIC PROBE

BACKGROUND OF THE INVENTION

The present invention relates to examination probes and, more particularly, to thin-film ultrasonic probes.

An ultrasonic probe is used to examine items such as manufactured parts by transmitting ultrasonic signals to the item and measuring a reflected signal returned by the item to the probe. Conventional probes typically include a transducer having a single crystal that creates the outgoing ultrasonic signals and measures the signals returned to the transducer. To facilitate the transmission of signals between conventional probes and the item being examined, the item is often wetted with water where the probe will be moved. The ultrasonic signals more easily transfer from the transducer to the item by way of the water disposed between the probe and the item. Without such a coupling fluid, some of the signals leaving the transducer would not reach the item, instead being reflected back to the transducer by a gap of air that may exist between the probe and the item. Ultrasonic signals reflect at interfaces where the density of transfer media decreases sufficiently, such as the case between a solid such as metal and a gas such as air, because the signals propagate through the path of least resistance, which may include remaining in the denser media. Such unwanted reflections confuse item examination by being confused with intended reflections from the item. Further, without a coupling fluid, some of the signals that do make it to the item may not return to the transducer as intended because they are reflected back toward the item at the previously mentioned air gap. In one conventional method, a spray bottle is used to repeatedly spray water on the item ahead of the probe as the probe is moved along a surface of the item.

The conventional method of frequently applying water to the item using external devices such as a spray bottle is tedious and hinders the examination process. For example, because the water must be applied as the probe is moved and the existence of a sufficient and consistent amount of water between the probe and the item cannot be ensured, a substantial amount of water must be applied and the probe must be moved slowly.

When examining items, it is often desired to examine edges of the item. However, when a portion of conventional probes is moved over an edge, any coupling fluid that was disposed beneath the portion of the probe moved beyond the edge falls over the edge leaving no coupling fluid adjacent that portion. When coupling fluid is absent from the over-the-edge portion of the probe, the fluid between the probe and the item adjacent the edge will tend to also flow over the edge. When this happens, the probe is unable to accurately determine characteristics of the item adjacent the edge. For example, the conventional probe cannot distinguish whether a signal reflected back to the transducer from air below the probe indicates the signal was reflected from air beneath the probe beyond an item edge or air caused by a lack of coupling fluid between the probe and the item because the fluid there flowed over the edge.

Further, it is difficult to accurately determine characteristics of item edges using a single crystal transducer. Depending on the positioning of the crystal on the probe, a good amount of the probe could be moved over the edge without the transducer knowing. Also, when the single crystal transducer does register that there is no item below the part, it is difficult to accurately identify the location of the crossed edge. In addition, with a single crystal transducer, the transducer may prematurely determine that the crystal is over an edge when the signal path has actually encountered an area over the item where the coupling fluid already began flowing over the edge as described. A probe and method of using it are needed that improve the coupling of probes to items being examined allowing reliable, expedient, and accurate evaluation of item characteristics including at their edges.

BRIEF SUMMARY OF THE INVENTION

The present invention relates to an ultrasonic probe for examining an item. The probe includes a body having a contact surface adapted for contacting the item when being examined and an ultrasonic transducer attached to the body and spaced from the contact surface. The probe further includes a spacer positioned in the body between the transducer and the contact surface for spacing the transducer from the item when being examined. The spacer includes a coupling surface facing the item when being examined and a transducer surface facing the transducer. The probe also includes a fluid outlet positioned adjacent the coupling surface of the spacer for delivering coupling fluid to the coupling surface as a film so that the coupling fluid tends to maintain contact with the spacer due to surface tension after the fluid is delivered through the outlet.

In another aspect, the present invention relates to a method for examining an item using an ultrasonic probe that includes a body having a contact surface and a fluid channel extending between a fluid inlet and a fluid outlet in the contact surface, a spacer having a coupling surface adjacent the contact surface, and an ultrasonic transducer connected to the body adjacent the spacer. The method includes positioning the contact surface of the probe body in contact with a contact surface of the item and delivering coupling fluid to the coupling surface of the spacer by way of the fluid channel to form a film of the coupling fluid on the coupling surface. The method further includes producing ultrasonic signals using the transducer and propagating the signals through the spacer and to the part. The method also includes moving the probe along the contact surface of the item and determining characteristics of the item based on ultrasonic signals reflected from the item back to the transducer.

Other aspects of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE INVENTION

Figure 1:
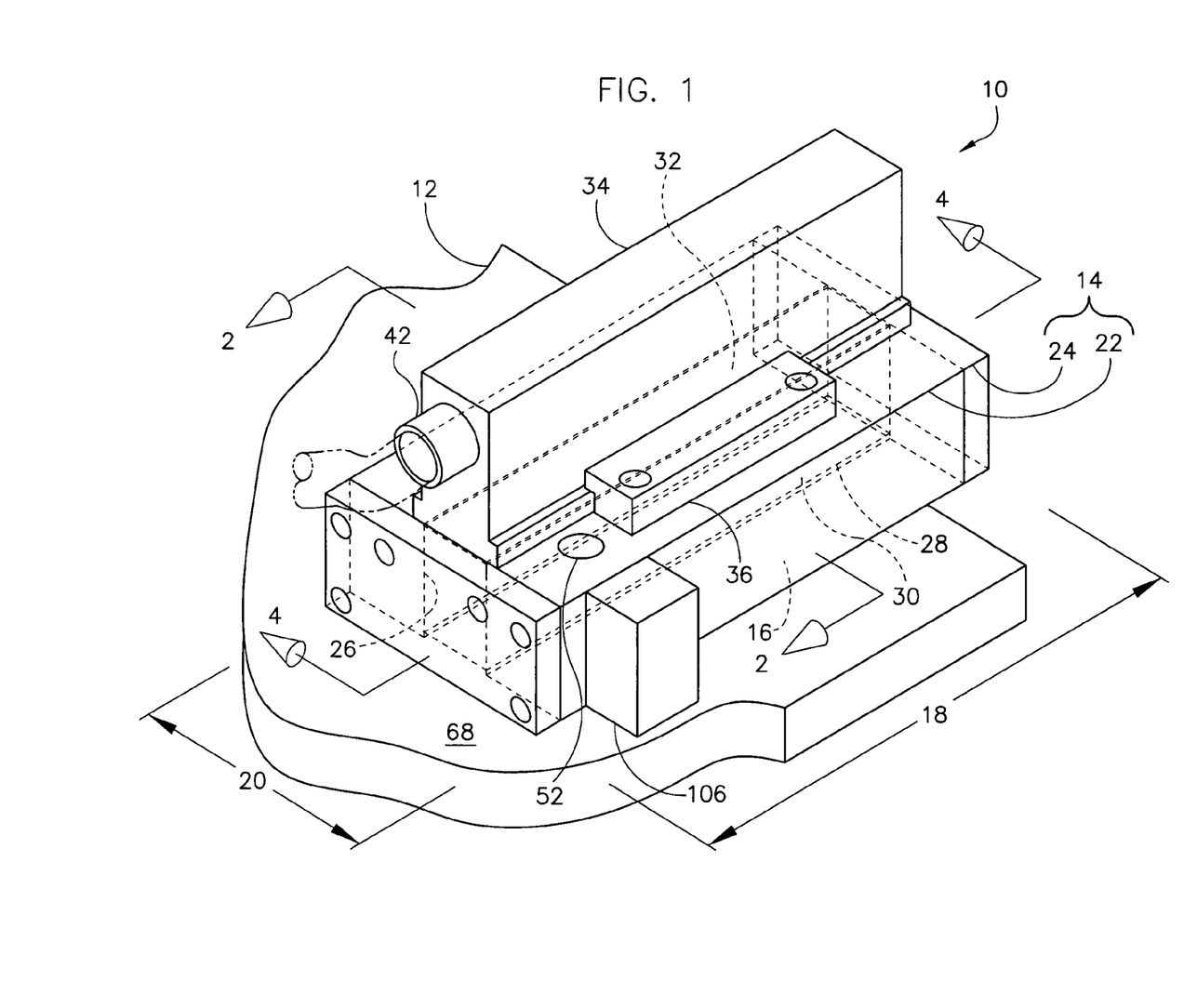
FIG. 1 is a perspective of an ultrasonic probe according to the present invention.

Referring to the figures, and more particularly to FIG. 1, an ultrasonic probe according to the present invention is designated in its entirety by reference number 10. The probe 10 is used to examine an item such as a manufactured part 12. Although the probe 10 may be used to examine other parts 12 without departing from the scope of the present invention, in one embodiment the probe is used to examine parts of an aircraft or other vehicle. The probe 10 includes a body 14 having a contact surface 16 adapted for contacting the part 12 during examination. Although the body 14 may have other lengths 18 without departing from the scope of the present invention, in one embodiment the body has a length of between about 3 inches and about 6 inches. Although the body 14 may have other widths 20 without departing from the scope of the present invention, in one embodiment the body has a width of between about 2 inches and about 3 inches. In one embodiment, the body 14 is made of a low-friction material so the probe 10 can easily slide across the part 12. Although the body 14 may be made of other materials without departing from the scope of the present invention, in one embodiment the body is made of a polymer. In a particular embodiment, the body 14 is made of Delrin, a synthetic low-friction polymer. Delrin is a federally registered trademark of E. I. du Pont de Nemours and Company Corporation of Wilmington, Del. The body 14 has opposite sides 22 and opposite ends 24 that form a cavity 26 between them. The sides 22 and the ends 24 may be formed integrally or separately. The probe 10 further includes a delay line or spacer 28 positioned in the cavity 26 of the body 14. The spacer 28 may be formed integrally with the body 14 or separately from it. The spacer 28 includes a coupling surface 30 adjacent the contact surface 16 and facing the part 12 when the probe 10 is being used to examine the part and a transducer surface 32 opposite the coupling surface.

The probe 10 also includes one or more transducers 34 attached to the body 14 adjacent the spacer 28. More particularly, the transducer 34 is positioned adjacent the transducer surface 32 of the spacer 28. The transducer 34 may be attached to the body 14 in various ways. In one embodiment, the transducer 34 is attached to the body 14 by a hold-down clamp 36 connected to the body and including a flange 38 that engages a corresponding lip 40 of the transducer. The transducer 34 produces signals with which the part 12 is examined. The signals are transmitted from the transducer 34 through the spacer 28 and part 12 and back through the part and spacer to the transducer. The transducer 34 includes or is configured for connection to a controller (not shown) and a power source (not shown). For example, the transducer 34 may include a control port 42 for connecting the transducer to an external controller. The controller manages transducer 34 signal output and interprets signals received by the transducer. Although other controllers may be used without departing from the scope of the present invention, in one embodiment the controller is an omniscan controller, available from Olympus-NDT, Inc., of Waltham, Mass. Although the transducer 34 may produce other types of signals without departing from the scope of the present invention, in one embodiment the transducer produces ultrasonic signals. The transducer 34 may include one or more crystals (not shown) producing the ultrasonic signals. As will be apparent by those skilled in the art, the crystals produce ultrasonic signals by oscillating in response to voltage input to them. The crystals also sense the signals that reflect back to the transducer from the part 12 or otherwise for determining part characteristics, such as size, shape, and interior imperfections (not shown). Examples of interior imperfections the transducer 34 may sense include delaminations, or unwanted separations between layers (not shown) of the part, and porosity outside of a predetermined range.

In one embodiment, the transducer 34 includes an array or matrix of crystals (not shown in detail). Although such a transducer 34 array may include other numbers of crystals, in one embodiment the array contains between 16 and 128 crystals. For example, in one embodiment the array includes 64 crystals. Although other transducers 34 may be used without departing from the scope of the present invention, in one embodiment the transducer is a phased-array transducer, available from Olympus-NDT, Inc., of Waltham, Mass.

Figure 2:
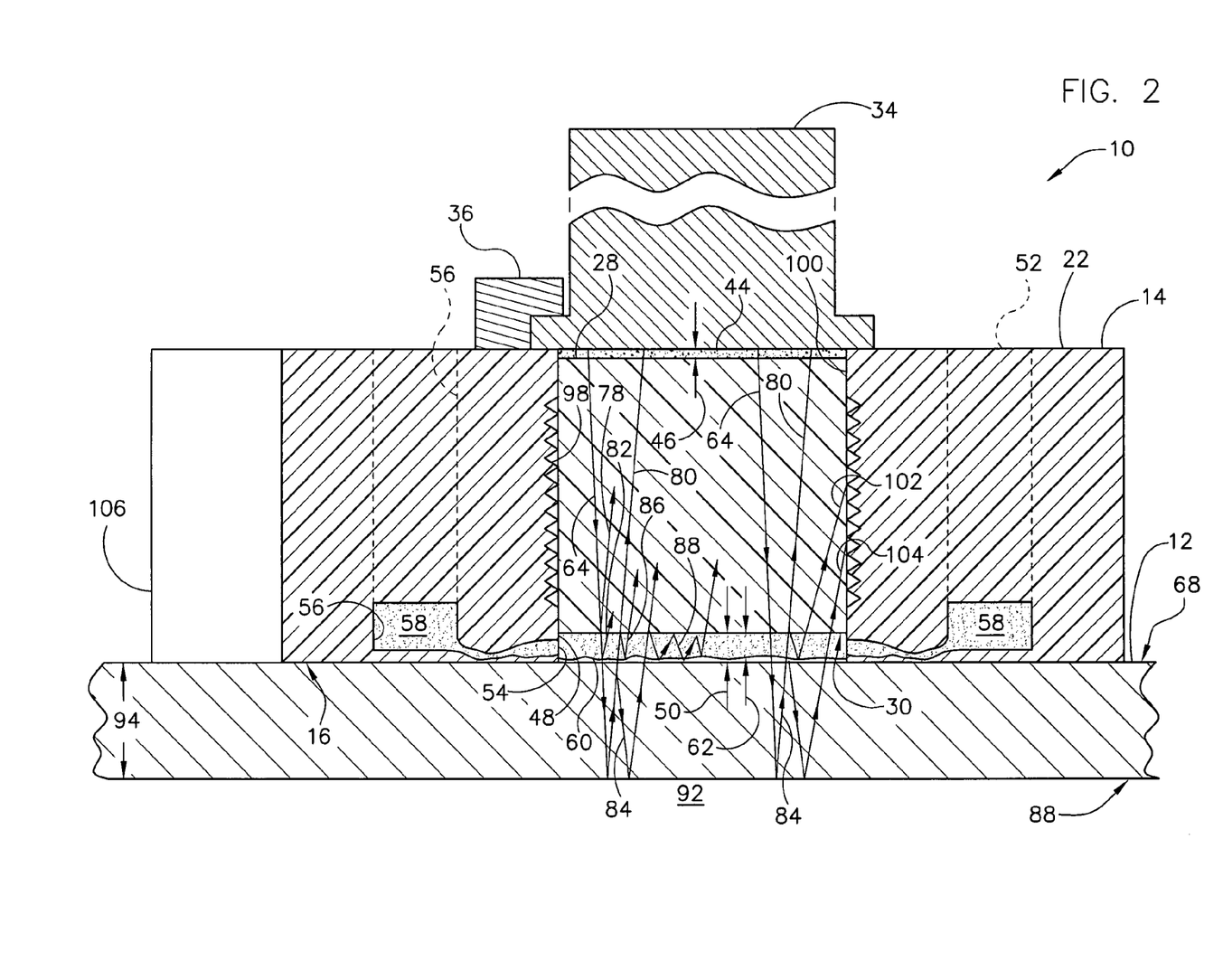
FIG. 2 is a cross section of the probe taken along line 2-2 of FIG. 1.

As shown in FIG. 2, the probe 10 may include a thin coupler 44 disposed between the transducer 34 and the spacer 28 to facilitate transmission of ultrasonic signals between the transducer and the spacer. Although other types of couplers 44 may be used without departing from the scope of the present invention, in one embodiment the coupler is a grease-like material, such as a commercially available ultragel. Although the layer of coupler 44 may have other thicknesses 46 without departing from the scope of the present invention, in one embodiment the layer of coupler has a thickness of between about 0.01 inches and 0.10 inches.

Figure 3:
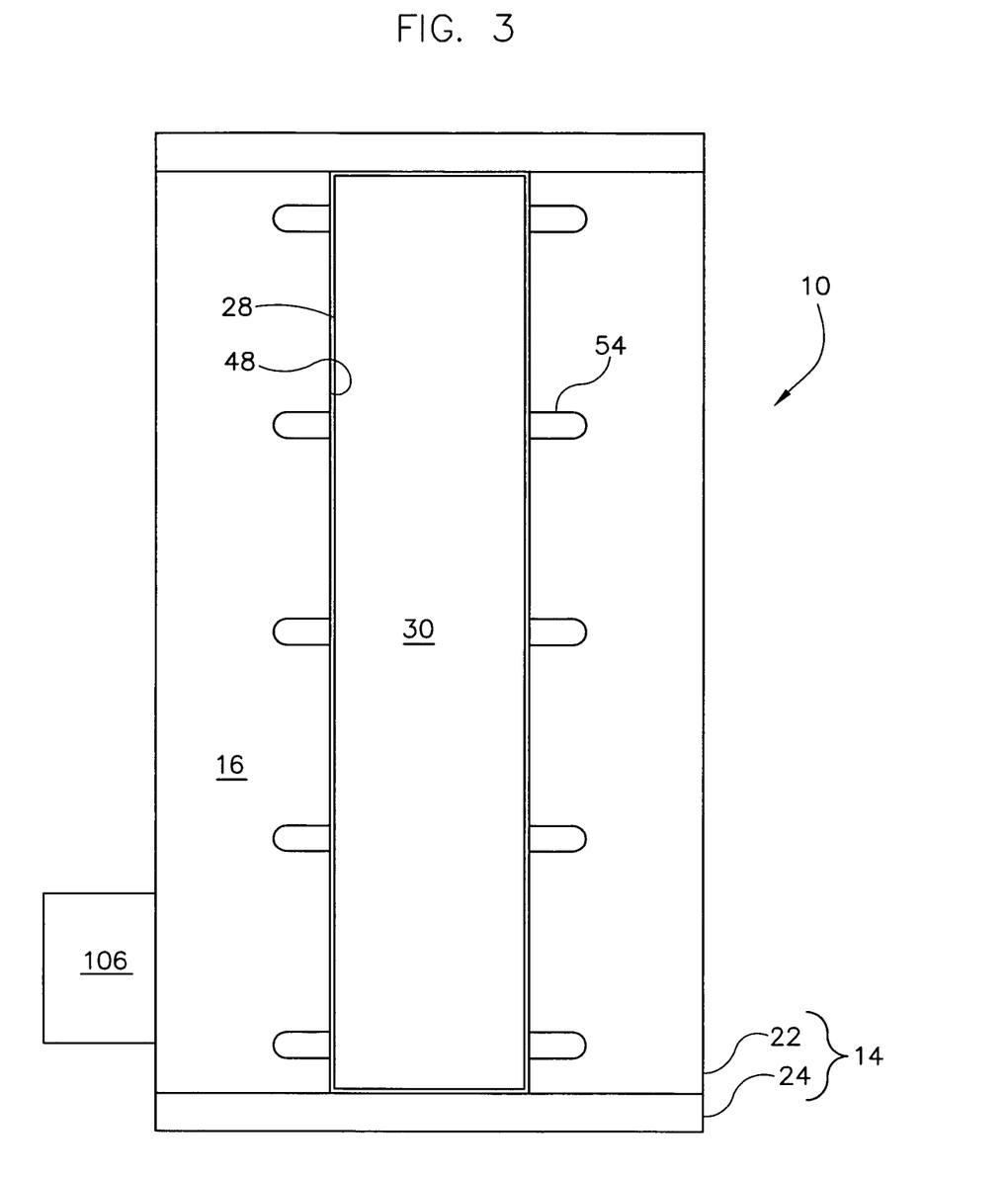
FIG. 3 is a bottom view of the probe.

The coupling surface 30 of the spacer 28 is offset from the contact surface 16 of the body 14 to form a recess 48. Although the recess 48 may have other depths 50 without departing from the scope of the present invention, in one embodiment the recess has a depth of between about 0.01 inches and about 0.05 inches. The probe 10 further includes a coupling fluid inlet 52 and a coupling fluid outlet 54 connected by a coupling fluid channel 56. The fluid inlet 52 is configured to be connected to an external fluid source (not shown). The probe 10 may include multiple fluid inlets 52 and may include multiple fluid outlets 54 distributed around the recess 48. For example, as shown in FIG. 3, the probe 10 may include ten fluid outlets 54, five outlets aligned along each side of the recess 48 adjacent the spacer 28. As shown in FIG. 2, the fluid outlets 54 may be positioned in the contact surface 16 of the body 14 and are configured so that, during operation of the probe 10, coupling fluid 58 channeled to the outlets from the fluid inlets 52 is delivered to the recess 48 so it contacts the coupling surface 30. For example, each fluid outlet 54 may be configured so coupling fluid 58 exits the outlet at an angle between about vertically downward (i.e., 90° with the contact surface 16) and horizontally inward in a general direction of the spacer 28 to facilitate contact between the fluid and the coupling surface 30 during operation of the probe. Although other coupling fluids 58 may be used without departing from the scope of the present invention, in one embodiment the coupling fluid is water.

Figure 4:
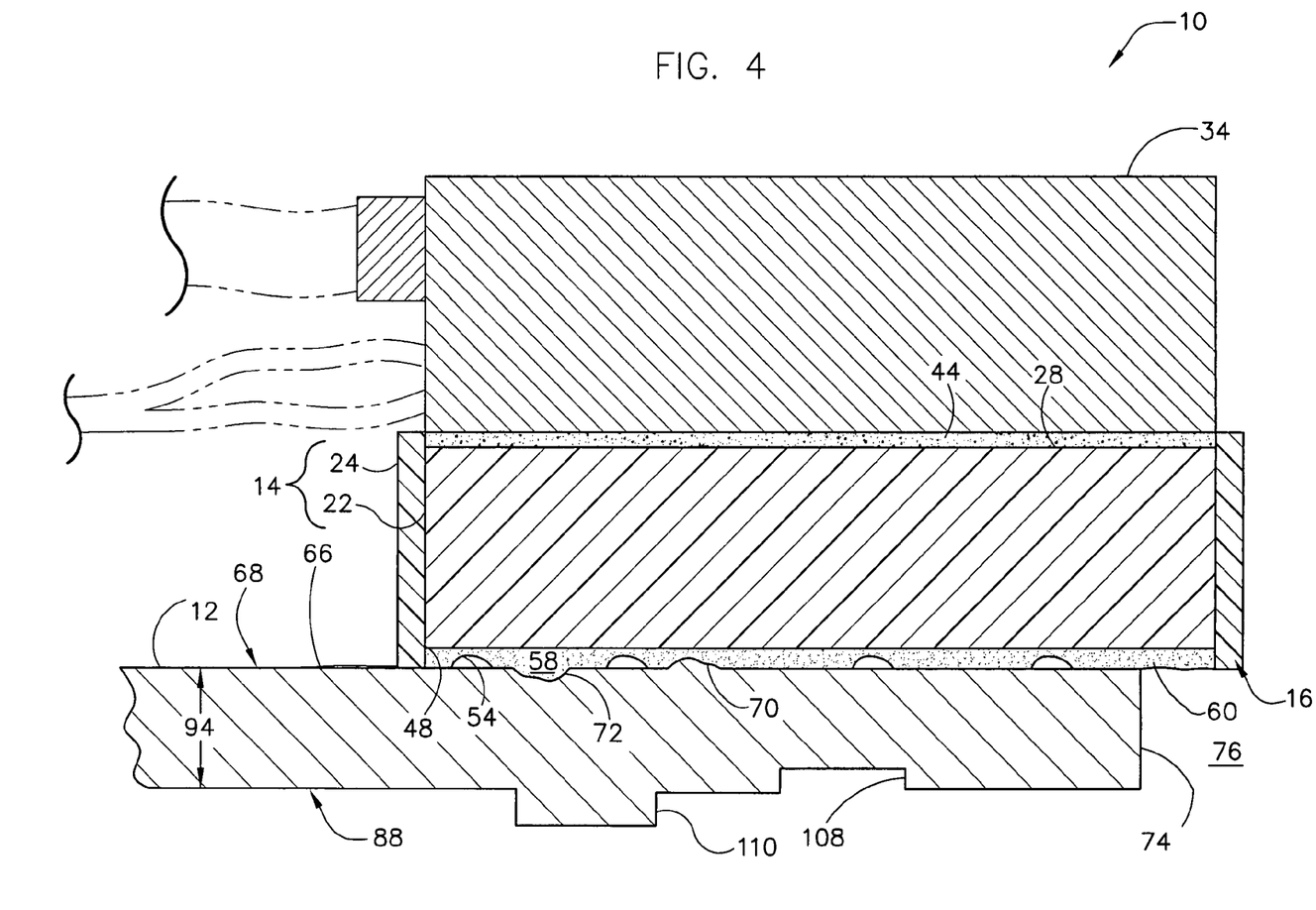
FIG. 4 is a cross section of the probe taken along line 4-4 of FIG. 1.

During operation of the probe 10, coupling fluid 58 delivered to the recess 48 and against the coupling surface 30 of the spacer 28 tends to adhere to and maintain contact with the coupling surface due to tension between the fluid and the coupling surface. The fluid 58 adhering to the coupling surface 30 forms a thin fluid film 60. In one embodiment, a thickness 62 of the film 60 is generally the same as the depth 50 of the recess 48. As will be appreciated by those skilled in the art, the fluid film 60 coupling the spacer 28 to the part 12 facilitates transition of ultrasonic signals 64 between the two. As shown in FIG. 4, some of the fluid 66 from the film 60 stays with the part 12 as the probe 10 moves along the part. This residual fluid 66 is replaced in the recess 48 by additional fluid 58 channeled to the recess 48 through the fluid outlet 54. The fluid 58 can be fed to the recess 48 continuously or intermittently and at various rates without departing from the scope of the present invention. Feeding fluid 58 to the recess 48 removes the need for external devices, such as spray bottles, to create the coupling between the spacer 28 and the part 12. Due to its fluid nature, the film 60 generally connects a contact or upper surface 68 of the part 12 to the spacer 28 uninterrupted across the coupling surface 30. The generally continuous fluid connection between the spacer 28 and part 12 will remain intact even when the upper surface 68 of the part 12 has small protrusions 70 and/or small depressions 72. When the probe 10 is moved over a small protrusion 70 in the part surface 68, film 60 deforms around the protrusion to absorb it. When the probe 10 is moved over a small depression 72 in the part surface, the film 60 extends into the depression to fill it. In these ways, the fluid film 60 maintains a generally continuous connection between the spacer 28 and the part 12 despite discontinuities in the part surface 68.

The fluid film 60 will also remain in the recess 48 and against a substantial entirety of the coupling surface 30 of the spacer 28 when the probe 10 is moved over an edge 74 of the part 12. That is, because of its thinness and associated fluid dynamics, the film 60 maintains its general shape and position within the recess 48 and against the coupling surface 30 despite the probe 10 being moved to a position where the part does not completely underlie the recess and film. The edge 74 can be an edge at an end of the part 12, as shown in FIGS. 1 and 4, or an edge of a large void in the part surface 68. Maintaining the coupling fluid 58 throughout the recess 48 when the probe 10 crosses an edge 74 is important for determining part 12 characteristics at and adjacent the edge. If the coupling fluid 58 did not remain in the recess 48 when the probe 10 crossed the edge 74, the transducer 34 would receive mixed signals about exactly what underlies the probe near and at the edge. That is, many of the ultrasonic signals 64 (shown in FIG. 2) leaving the transducer 34 would get scrambled in the fluid 58 exiting the recess 48 and flowing over the edge 74 and the signals that did get reflected back to the transducer would not be sufficient to allow the user to accurately determine characteristics of the part at and near the edge.

Further, loss of fluid 58 from the coupling film 60 beyond the edge 74 could result in losses of fluid from the film at locations of the probe 10 adjacent the edge under which the part 12 still lies. Such additional coupling fluid 58 loss adds to the inaccurate reflected signals the transducer will measure. For example, as described in the Background of the Invention Section above, it is difficult to distinguish whether a signal reflected back to the transducer 34 from air below the probe indicates the signal was reflected from air beneath the probe beyond a part 12 edge 74 or air caused by a lack of coupling fluid between the probe 10 and the part because the fluid 58 there flowed over the edge. On the other hand, when the fluid film 60 is maintained in the recess 48 continuously across the coupling surface 30 of the spacer 28 whether the probe 10 is positioned partly or completely over the part 12, the generally uniform coupling layer beneath the spacer 28 allows the controller to better interpret the signals returned to the transducer 34. The controller will know whether changes in the quality and/or timing of returned signals result from changes in part characteristics or a part 12 edge 74. When the part 12 does not underlie a portion of the recess 48, the ultrasonic signals 64 transmitted from the transducer 34 and through the spacer 28 and film 60 will reflect from air 76 below the film back to the transducer in a generally uniform manner due to the generally uniform shape of the film. More uniform reflected signals provide a more accurate indication of a shape and location of the part 12 including its edge 74.

The spacer 28 is positioned in the body 14 between the transducer 34 and the contact surface 16 for spacing the transducer from the part 12 when being examined. A material and size of the spacer 28 controls a manner in which the ultrasonic signals 64 are transmitted between the transducer 34 and the part 12. The spacer 28 is made of materials and sized so unwanted ultrasonic signals, such as signals 78 (shown in FIG. 2) reflected from the coupling surface 30 of the spacer 28, are not confused with the signals 80 transmitted through the part 12 and back to the transducer 34 as intended. To avoid such confusion, the controller must be able to distinguish between signals 80 returning to the transducer 34 as intended and signals 78, 82, 84, 86, 88 reflected back to the transducer in other ways.

The probe 10 may be used to determine characteristics of the part 12, such as qualities of a lower surface 90 of the part, by transmitting ultrasonic signals 64 through the spacer 28 and into the part. Properly transmitted signals 64 reflect back toward the transducer 34 from the lower surface 88 of the part 12 as the signals encounter the air 92 adjacent that surface. The reflected signals 80 propagate back through the part 12, the coupling film 60, and the spacer 28 and to the transducer 34. The controller determines characteristics of the part 12, such as shape and/or size, based on a timing and/or strength of the returned signals 80. The controller may also consider the location at which a reflected signal 80 returns to the transducer 34. Signals 78, 82, 84, 86, 88 reflected back to the transducer 34 in unintended ways muddle transducer feedback, which interferes with the ability of the controller to accurately determine part 12 characteristics.

Signals reflected back to the transducer 34 in unintended ways include signals 78 reflected at the coupling surface 30, signals 82 reflected between the coupling film 60 and the part 12, signals 84 reflected at the lower surface 90 of the part 12 as intended but then reflected back down between the film and part, signals 86 reflected at the lower surface 90 of the part 12 as intended but then reflected back down at the coupling surface, and signals 88 that echo or get temporarily trapped between surfaces 30, 68, 86. For a part 12 having a thickness 90 in a known range, the controller can be programmed to expect the intended reflected signals 80 to return to the transducer at a particular time and strength. The controller can distinguish between intended reflected signals 80 and unintended reflected signals 78, 82, 84, 86, 88 based on the timing and/or strength of the returned signals 80. The controller can be programmed to determine that a slight deviation from the expected time and/or strength of a returned signal 80 is due to a small change in the shape of the part 12 or a small error in the part. The controller can be programmed to conclude that a large deviation from an expected time and strength indicates either a large change in part shape, a large error in the part, or that the signal is an unintended reflection 78, 82, 84, 86, 88. By being able to distinguish between intended reflected signals 80 and unintended reflected signals 78, 82, 84, 86, 88, the controller can better consider the intended reflected signals to accurately determine part 12 characteristics.

Figure 5:
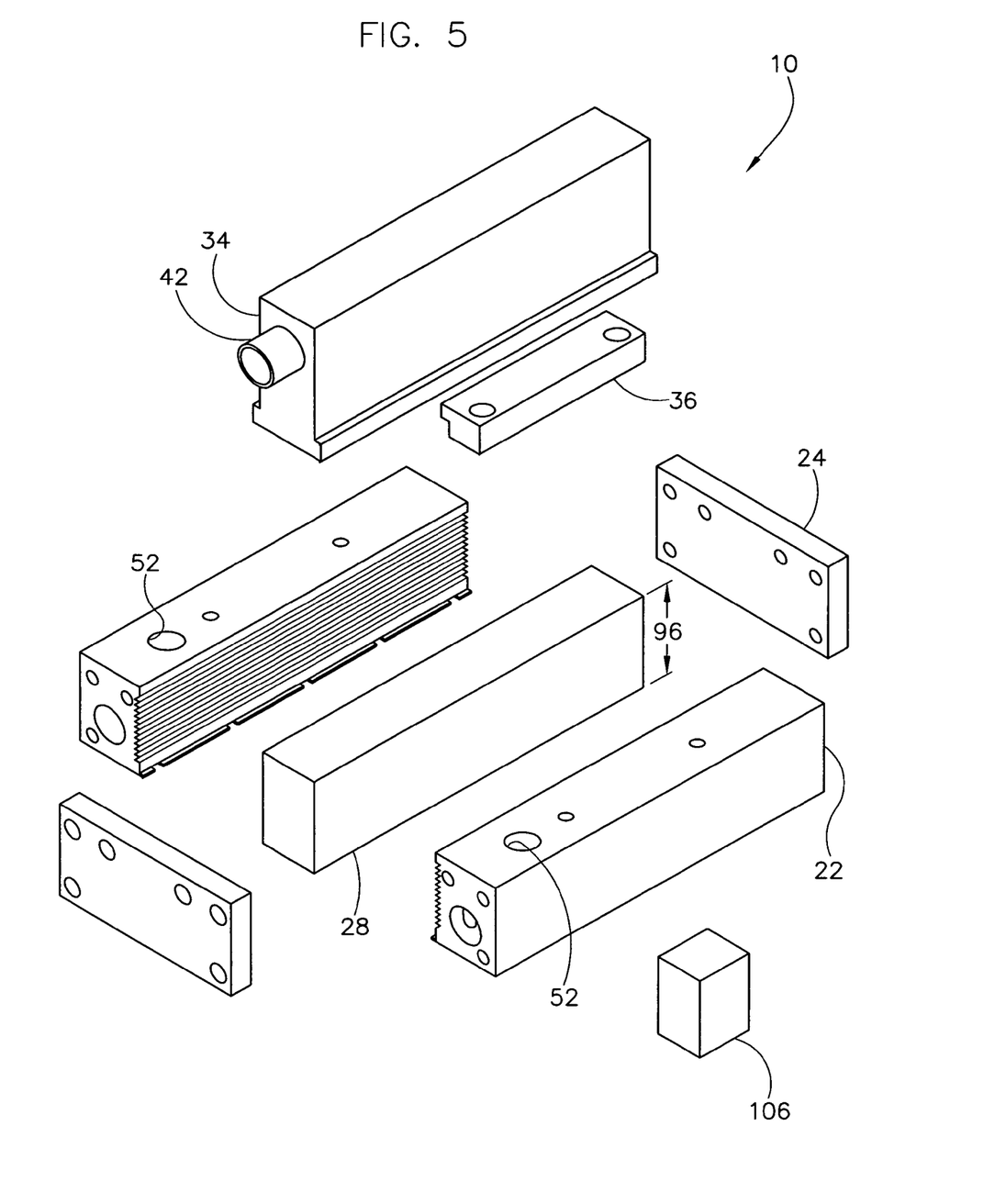
FIG. 5 is a fragmented view of the probe.

The spacer 28 is sized and made of materials that enable the controller to better distinguish intended reflected signals 80 from unintended reflected signals 78, 82, 84, 86, 88. The controller considers the speed at which signals 64 are expected to travel through the spacer 28 and the part 12 and back to the transducer 34 for a given spacer material, spacer size, part size, and part material. The controller may also consider dimensions and a type of the coupling fluid 58 used. Various spacer 28 sizes and materials can be used to optimize the ability of the controller to distinguish the intended return signals 80 from the unintended return signals 78, 82, 84, 86, 88 for a given part 12 size and material. The probe 10 can be used with any one of multiple differently sized spacers 28. Each of the differently sized spacers 28 can correspond to a part 12 having a thickness 94 in a particular range. For example, in one embodiment, a spacer having a height 96 (shown in FIG. 5) of between about 0.9 inches and about 1.0 inch is used when the thickness 90 of the part 12 being examined is between about 0.07 inches and about 0.68 inches. Although the probe 10 may be used with a spacer 28 outside of the size range determined to correspond best to the particular part 12 being examined, using the preferred spacer size facilitates the ability of the controller to distinguish between wanted return signals 80 and unwanted return signals 78, 82, 84, 86, 88 and more accurately determine part qualities.

Along with the size of the spacer 28, the material of the spacer affects propagation of signals 64 through it. Thus, the size and material of the spacer 28 are considered in selecting the proper spacer to use for a particular application. In one embodiment, the spacer 28 material has a sonic velocity that is nearly the same as that of water. Although the spacer 28 may have other sonic velocities without departing from the scope of the present invention, in one embodiment the spacer has a sonic velocity of between about 0.05 inches/microsecond and about 0.07 inches/microsecond. In one embodiment, the spacer 28 is made of a solid material or a semisolid material. A semi-solid is a material having qualities of both a solid and a liquid. Although the spacer 28 may be made of other materials without departing from the scope of the present invention, in one embodiment the spacer is made of aqueline or plexiglass. Aqueline is an elastomeric or rubber-like material available from Olympus-NDT, Inc., of Waltham, Mass.

The probe 10 may also include grooves 98 extending generally in parallel along inside walls 100 of the body 14 so the walls are not completely smooth. The grooves minimize the amount of stray signals 102, 104 that return to the transducer 34. Instead of grooves 98, the walls 100 may include protrusions, depressions, corrugations, ribs, and/or the like (not shown). The grooves 98 absorb stray signals 102, 104 incident upon the walls 100. If not for the grooves 98, the stray signals 102, 104 would reflect off of the walls 100 and to the transducer 34 and be considered by the controller. The controller would likely confuse such stray signals 102, 104 with intended reflected signals 80, thereby muddling the ability of the controller to accurately determine part 12 characteristics.

The probe 10 may also include an encoder 106 (shown in FIGS. 1 and 2) mounted on the body 14. The encoder 106 is used to measure probe 10 displacement with respect to the part 12 when the probe is moved along the upper part surface 68. The controller can use the displacement measurements from the encoder 106 in various ways. In one embodiment, the controller can use the displacement measurements to create a map (not shown) of the part 12 including part characteristics determined by the transducer 34 at the various positions identified by the encoder 106. The controller may also compare measured part 12 characteristics to specification characteristics to determine how true a part is to design. For example, a controller may be programmed to expect the undersurface 88 of the part 12 to have an indentation 108 (shown in FIG. 4) and a projection 110 at respective distances from a starting edge (not shown) of the part. Thus, when the probe 10 moves over the indentation 108 and/or the projection 110, the controller will expect the intended return signals 80 to return accordingly, such as an expected timing and signal strength. The encoder 106 can also be used to determine a rate of probe 10 movement with respect to the part 12. This rate can be used to control, for example, the rate at which coupling fluid 58 is fed to the recess 48.

For use, the probe 10 is connected to the fluid source (not shown), such as a source of water, by way of the fluid inlet 52. If the controller is an external controller, the probe 10 is connected to the controller by way of the controller port 42. Then, the contact surface 16 of the probe 10 body 14 is positioned in contact with a contact surface 68 of the part 12. Before or after the probe 10 is placed in contact with the part 12, coupling fluid 58 is delivered from the fluid source to the recess 48 by way of the fluid inlet 52, the fluid channel 56, and fluid outlet 54. Delivering the coupling fluid 58 to the recess 48 may include controlling a rate at which the fluid passes through the fluid channel 56 and out of the outlet 54. The fluid 58 delivered to the recess 48 forms the thin film 60 as it adheres to the coupling surface 30 of the spacer 28 due to surface tension. The film 60 is maintained across the coupling surface 30 of the spacer 28 whether the probe 10 is being moved over a smooth surface, protrusions 70, depressions 72, and/or an edge 74 of the part 12 so a portion of the spacer is positioned above the part and a portion of the spacer is not positioned above the part.

Using the probe 10 further includes producing signals 64 using the transducer 34. The signals 64 are transmitted from the transducer 34, through the spacer 28, through the coupling fluid film 60, and into the part 12. The probe 10 is moved along the part 12 while the coupling fluid 58 is delivered to the recess 48 and the ultrasonic signals 64 are transmitted. The signals produced by the transducer 34 that are reflected back to the transducer from the part 12 are sensed by the transducer. The controller determines characteristics of the part 12 based on the signals sensed by the transducer 34. Determining part 12 characteristics may include determining a location and/or dimensions of an indentation 108, a projection 110, and/or an edge 74 of the part 12. Although the probe 10 may be moved along the part surface 68 at other rates while determining part characteristics using the transducer 34, in one embodiment the probe is moved along the part surface at a rate of between about 5 inches/second and about 16 inches/second while determining part characteristics using the transducer.

Probe 10 use may also include measuring displacement of the probe using the encoder 106 while the probe is moved along the part surface 68. The controller can consider the location of the probe 10 on the part 12, as determined by the encoder 106, in determining part characteristics. For example, as described above, the controller can use the displacement measurements from the encoder 106 to create a map (not shown) of the part 12 and may compare measured part characteristics to specification part shapes and/or dimensions. Further, the encoder 106 can be used to determine a rate of probe movement with respect to the part 12, which rate can be used to control, for example, the rate at which coupling fluid 58 is fed to the recess 48.

To more accurately determine part 12 characteristics, the spacer 28 material and size are selected so intended reflected signals 80 (shown in FIG. 2) are not confused with unintended reflected signals 78, 82, 84, 86, 88, as described above. As another way to more accurately determine part 12 characteristics, using the probe 10 may include absorbing stray signals 102, 104 by way of grooves 98 in the inside wall 100 of the body 14 so the stray signals are not returned to the transducer 34 and confused with intended reflected signals 80.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An ultrasonic probe for examining an item comprising:
 a body including a contact surface adapted for contacting the item when being examined and a cavity having opposite sides, each side having a plurality of grooves;

an ultrasonic transducer attached to the body and spaced from the contact surface;

a spacer positioned in the cavity between the transducer and the contact surface for spacing the transducer from the item when being examined, said spacer including a coupling surface facing the item when being examined and a transducer surface facing the transducer; and a fluid outlet positioned adjacent the coupling surface of the spacer for delivering coupling fluid to the coupling surface as a film so that the coupling fluid tends to maintain contact with the spacer due to surface tension after the fluid is delivered through the outlet.

2. An ultrasonic probe as set forth in claim 1 wherein the body comprises a polymer.

3. An ultrasonic probe as set forth in claim 1 wherein said spacer has a sonic velocity of between about 0.05 inches/microsecond and about 0.07 inches/microsecond.

4. An ultrasonic probe as set forth in claim 1 wherein each transducer includes an array of elements, each element including a crystal that oscillates to create ultrasonic signals with which the item is examined during operation of the probe.

5. An ultrasonic probe as set forth in claim 1 wherein said spacer and said body are separately formed.

6. An ultrasonic probe as set forth in claim 1 wherein said probe further includes an encoder mounted on the body for measuring displacement of the probe as it moves along a surface of the item during operation of the probe.

7. An ultrasonic probe as set forth in claim 1 wherein the body includes a cavity in which the spacer and the transducer are positioned.

8. An ultrasonic probe as set forth in claim 1 wherein said spacer includes a solid material.

9. An ultrasonic probe as set forth in claim 1 wherein said spacer includes a material selected from a group of materials including aqueline and plexiglass.

10. An ultrasonic probe as set forth in claim 1 wherein the coupling fluid passes through said outlet at an angle of between about 0° and about 90° with the contact surface of the probe in a general direction of the spacer to facilitate contact between the coupling fluid and the coupling surface of the spacer during operation of the probe.

11. An ultrasonic probe as set forth in claim 1 wherein said coupling surface of the spacer is offset from the contact surface of the body to form a recess through which said coupling fluid film moves during operation of the probe.

12. An ultrasonic probe as set forth in claim 11 wherein said fluid outlet includes multiple ports distributed around said recess.

13. An ultrasonic probe as set forth in claim 1 wherein said grooves extend in generally parallel along said sides.

14. A method for examining an item using an ultrasonic probe including a body having a contact surfaces, a fluid channel extending between a fluid inlet and a fluid outlet in the contact surface, and a cavity having opposite sides, each side having a plurality of grooves, the probe further including a spacer positioned in the cavity and having a coupling surface adjacent said contact surface, the probe further including an ultrasonic transducer connected to the body adjacent said spacer, the method comprising:

positioning the contact surface of the probe body in contact with a contact surface of the item;

delivering coupling fluid to the coupling surface of said spacer by way of said fluid channel to form a film of the coupling fluid on the coupling surface;

producing ultrasonic signals using said transducer;

propagating said signals through the spacer and to the item;

absorbing stray ultrasonic signals by way of said grooved sides;

moving the probe along the contact surface of the item; and determining characteristics of the item based on ultrasonic signals reflected from the item back to the transducer.

15. A method as set forth in claim 14 further comprising connecting said probe to an external fluid source by way of said fluid inlet.

16. A method as set forth in claim 14 further comprising connecting said transducer to an external controller.

17. A method as set forth in claim 14 further comprising controlling a rate at which said coupling fluid passes through said fluid channel.

18. A method as set forth in claim 14 wherein said moving includes moving the probe along the item surface at a rate of between about 5 inches/second and about 16 inches/second while performing said determining step.

19. A method as set forth in claim 14 wherein said probe includes an encoder mounted on the body and said method further comprises measuring displacement of said probe as it moves along the item surface using said encoder during said moving.

20. A method as set forth in claim 14 wherein:

said moving includes moving said probe over an edge of the item so a portion of the probe body and a portion of the spacer are positioned above the item and a portion of the body and a portion of the spacer are not positioned above the item;

said delivering includes maintenance of said coupling fluid film across the coupling surface of the spacer while the probe is partially positioned over the edge of the part; and said determining includes determining a location and/or dimensions of said item edge.

21. An ultrasonic probe comprising:

a probe body having a contact surface and a cavity that is open at the contact surface, the cavity having opposite sides, each side having a plurality of grooves;

an ultrasonic transducer carried by the body; and a spacer within the cavity, the spacer having a first surface acoustically coupled the transducer, and a second surface within the cavity, the spacer for propagating an acoustic signal between the transducer and the second surface;

the second surface spaced apart from the contact surface.

* * * * *

UNITED STATES PATENT AND TRADEMARK OFFICE
CERTIFICATE OF CORRECTION

PATENT NO. : 7,637,163 B2 Page 1 of 1
APPLICATION NO. : 11/345904
DATED : December 29, 2009
INVENTOR(S) : Fetzer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 956 days.

Signed and Sealed this

Ninth Day of November, 2010

David J. Kappos
*Director of the United States Patent and Trademark Office*